(12) United States Patent
Cameron

(10) Patent No.: US 8,718,734 B2
(45) Date of Patent: May 6, 2014

(54) NON-INVASIVE POLARIMETRIC APPARATUS AND METHOD FOR ANALYTE SENSING IN BIREFRINGENT MEDIA

(75) Inventor: Brent D. Cameron, Waterville, OH (US)

(73) Assignee: The University of Toledo, Toledo, OH (US)

( * ) Notice: Subject to any disclaimer, the term of this patent is extended or adjusted under 35 U.S.C. 154(b) by 691 days.

(21) Appl. No.: 12/741,289

(22) PCT Filed: Nov. 7, 2008

(86) PCT No.: PCT/US2008/082742
§ 371 (c)(1),
(2), (4) Date: May 13, 2010

(87) PCT Pub. No.: WO2009/061993
PCT Pub. Date: May 14, 2009

(65) Prior Publication Data
US 2010/0234704 A1    Sep. 16, 2010

Related U.S. Application Data

(60) Provisional application No. 61/002,195, filed on Nov. 7, 2007, provisional application No. 61/005,120, filed on Dec. 3, 2007.

(51) Int. Cl.
*A61B 5/00* (2006.01)
*A61B 5/1455* (2006.01)
*A61B 5/145* (2006.01)

(52) U.S. Cl.
CPC .............. *A61B 5/00* (2013.01); *A61B 5/0002* (2013.01); *A61B 5/1455* (2013.01); *A61B 5/14555* (2013.01); *A61B 5/14532* (2013.01); *A61B 5/14558* (2013.01)

USPC .......................................................... 600/319

(58) Field of Classification Search
CPC .......................................................... A61B 5/00
USPC ................................................. 600/310, 319
See application file for complete search history.

(56) References Cited

U.S. PATENT DOCUMENTS 5,209,231 A    5/1993    Cote et al.
5,303,709 A    4/1994    Dreher et al.
(Continued)

FOREIGN PATENT DOCUMENTS

WO    2005067522 A2    7/2005

OTHER PUBLICATIONS

Marcel J. Goetz, Jr., Martin D. Fox, MD. PH.D, and Robert B. Northrop, PH.D, "Microdegree Polarimetry Using a Diode Laser for Glucose Detection," IEEE, 1992, pp. 97-98.*
(Continued)

*Primary Examiner* — Clayton E Laballe
*Assistant Examiner* — Kevin Butler
(74) *Attorney, Agent, or Firm* — MacMillian, Sobanski & Todd, LLC

(57) ABSTRACT

A noninvasive polarimetric apparatus used to measure levels of a substance in a sample in the presence of dynamically changing sample birefringence is provided. A polarization system generates multiple states of polarized light which interact with the sample. An analyzer system receives a signal from the sample and generates a secondary signal. This signal is detected and then processed to measure levels of a substance in a sample that may be have time varying birefringent components.

41 Claims, 10 Drawing Sheets

(56) References Cited

U.S. PATENT DOCUMENTS

| | | | |
|---|---|---|---|
| 5,710,630 A * | 1/1998 | Essenpreis et al. | 356/479 |
| 5,743,262 A * | 4/1998 | Lepper et al. | 600/316 |
| 5,788,632 A * | 8/1998 | Pezzaniti et al. | 600/316 |
| 6,246,893 B1 | 6/2001 | Gobeli | |
| 6,356,036 B1 * | 3/2002 | Zhou | 315/215 |
| 6,370,407 B1 | 4/2002 | Kroeger et al. | |
| 6,424,850 B1 * | 7/2002 | Lambert et al. | 600/319 |
| 6,704,106 B2 | 3/2004 | Anderson et al. | |
| 6,885,882 B2 * | 4/2005 | Cote et al. | 600/319 |
| 7,245,952 B2 | 7/2007 | Cameron | |
| 7,301,633 B2 * | 11/2007 | Gibbs et al. | 356/369 |
| 7,411,675 B2 * | 8/2008 | Matsumoto et al. | 356/364 |
| 7,438,855 B2 * | 10/2008 | Sota et al. | 422/82.09 |
| 7,502,111 B2 * | 3/2009 | Gibbs | 356/364 |
| 7,627,357 B2 * | 12/2009 | Zribi et al. | 600/319 |
| 2003/0223064 A1 | 12/2003 | Anderson et al. | |
| 2003/0225321 A1 * | 12/2003 | Cote et al. | 600/318 |
| 2003/0233036 A1 * | 12/2003 | Ansari et al. | 600/316 |
| 2005/0094144 A1 * | 5/2005 | Gibbs et al. | 356/365 |
| 2007/0055117 A1 * | 3/2007 | Alphonse | 600/310 |
| 2008/0033261 A1 * | 2/2008 | Zeller | 600/319 |

OTHER PUBLICATIONS

Sunghoon Jang, and Martin D. Fox, "Double Lock-In Concept for More Glucose Detection," IEEE, 1999, pp. 122-124.*

Purvinis, Georgeanne et al., Journal of Diabetes Science and Technology Noninvasive Polarimetric-Base Glucose Monitoring an in Vivo Study, vol. 5, Issue 2, Mar. 2011.*

Cameron et al., Diabetes Technology and Therapeutics, "Development of a Real-Time Corneal Birefringence Compensated Glucose Sensing Polarimeter", vol. 8, No. 2, 2006.*

Yamane, Ken et al, Proteome Analysis of Human Vitreous Proteins, The American Society for Biochemistry and Molecular Biology, Inc., 2003.*

A. Weber, "Relationship between Foveal Birefringence and Visual Acuity in Neovascular Age related Macular Degeneration", 2007, Nautre Publishing Group, 0950-222X/07.*

PCT International Search Report and the Written Opinion, PCT/US08/82742 filed Nov. 7, 2008, dated Jan. 6, 2009.

PCT International Preliminary Report, PCT/US20081082742 filed Nov. 7, 2008, dated May 20, 2010.

* cited by examiner

| Polarizing Components | Mueller Matrices |
|---|---|
| Vertical Polarizer (VP) | $\frac{1}{2}\begin{bmatrix} 1 & -1 & 0 & 0 \\ -1 & 1 & 0 & 0 \\ 0 & 0 & 0 & 0 \\ 0 & 0 & 0 & 0 \end{bmatrix}$ |
| Variable Retarder Modulator I (VRM1) | $\begin{bmatrix} 1 & 0 & 0 & 0 \\ 0 & \cos(2\phi_1)^2+(\sin(2\phi_1)^2*\cos(\delta(t))) & \sin(2\phi_1)*\cos(2\phi_1)*(1-\cos(\delta(t))) & -\sin(2\phi_1)*\sin(\delta(t)) \\ 0 & \sin(2\phi_1)*\cos(2\phi_1)*(1-\cos(\delta(t))) & \sin(2\phi_1)^2+(\cos(2\phi_1)^2*\cos(\delta(t))) & \cos(2\phi_1)*\sin(\delta(t)) \\ 0 & \sin(2\phi_1)*\sin(\delta(t)) & -\cos(2\phi_1)*\sin(\delta(t)) & \cos(\delta(t)) \end{bmatrix}$ |
| Variable Retarder Modulator II (VRM2) | $\begin{bmatrix} 1 & 0 & 0 & 0 \\ 0 & \cos(2\phi_2)^2+(\sin(2\phi_2)^2*\cos(\delta(t))) & \sin(2\phi_2)*\cos(2\phi_2)*(1-\cos(\delta(t))) & -\sin(2\phi_2)*\sin(\delta(t)) \\ 0 & \sin(2\phi_2)*\cos(2\phi_2)*(1-\cos(\delta(t))) & \sin(2\phi_2)^2+(\cos(2\phi_2)^2*\cos(\delta(t))) & \cos(2\phi_2)*\sin(\delta(t)) \\ 0 & \sin(2\phi_2)*\sin(\delta(t)) & -\cos(2\phi_2)*\sin(\delta(t)) & \cos(\delta(t)) \end{bmatrix}$ |
| Variable Retarder Modulator III (VRM3) | $\begin{bmatrix} 1 & 0 & 0 & 0 \\ 0 & \cos(2\phi_3)^2+(\sin(2\phi_3)^2*\cos(\delta(t))) & \sin(2\phi_3)*\cos(2\phi_3)*(1-\cos(\delta(t))) & -\sin(2\phi_3)*\sin(\delta(t)) \\ 0 & \sin(2\phi_3)*\cos(2\phi_3)*(1-\cos(\delta(t))) & \sin(2\phi_3)^2+(\cos(2\phi_3)^2*\cos(\delta(t))) & \cos(2\phi_3)*\sin(\delta(t)) \\ 0 & \sin(2\phi_3)*\sin(\delta(t)) & -\cos(2\phi_3)*\sin(\delta(t)) & \cos(\delta(t)) \end{bmatrix}$ |
| Anterior Corneal Retarder (AR) | $\begin{bmatrix} 1 & 0 & 0 & 0 \\ 0 & \cos(2\phi_A)^2+(\sin(2\phi_A)^2*\cos(\delta_A)) & \sin(2\phi_A)*\cos(2\phi_A)*(1-\cos(\delta_A)) & -\sin(2\phi_A)*\sin(\delta_A) \\ 0 & \sin(2\phi_A)*\cos(2\phi_A)*(1-\cos(\delta_A)) & \sin(2\phi_A)^2+(\cos(2\phi_A)^2*\cos(\delta_A)) & \cos(2\phi_A)*\sin(\delta_A) \\ 0 & \sin(2\phi_A)*\sin(\delta_A) & -\cos(2\phi_A)*\sin(\delta_A) & \cos(\delta_A) \end{bmatrix}$ |
| Sample (S) | $\begin{bmatrix} 1 & 0 & 0 & 0 \\ 0 & \cos(2\phi_R) & \sin(2\phi_R) & 0 \\ 0 & -\sin(2\phi_R) & \cos(2\phi_R) & 0 \\ 0 & 0 & 0 & 1 \end{bmatrix}$ |
| Posterior Corneal Retarder (PR) | $\begin{bmatrix} 1 & 0 & 0 & 0 \\ 0 & \cos(2\phi_P)^2+(\sin(2\phi_P)^2*\cos(\delta_P)) & \sin(2\phi_P)*\cos(2\phi_P)*(1-\cos(\delta_P)) & -\sin(2\phi_P)*\sin(\delta_P) \\ 0 & \sin(2\phi_P)*\cos(2\phi_P)*(1-\cos(\delta_P)) & \sin(2\phi_P)^2+(\cos(2\phi_P)^2*\cos(\delta_P)) & \cos(2\phi_P)*\sin(\delta_P) \\ 0 & \sin(2\phi_P)*\sin(\delta_P) & -\cos(2\phi_P)*\sin(\delta_P) & \cos(\delta_P) \end{bmatrix}$ |
| Horizontal Analyzer (HA) | $\frac{1}{2}\begin{bmatrix} 1 & 1 & 0 & 0 \\ 1 & 1 & 0 & 0 \\ 0 & 0 & 0 & 0 \\ 0 & 0 & 0 & 0 \end{bmatrix}$ |
| Laser (L) | $\begin{bmatrix} 1 \\ 0 \\ 0 \\ 0 \end{bmatrix}$ |

Figure 7 – Table 1

| Glucose Concentration | Azimuthal angle<br><br>anterior corneal retarder | Azimuthal angle<br><br>posterior corneal retarder | Retardance<br><br>anterior corneal surface | Retardance<br><br>posterior corneal surface |
|---|---|---|---|---|
| 100 mg/dl – 550 mg/dl<br><br>Steps: 50 mg/dl | π/90 – π/18 radians<br><br>Steps: π/90 radians | π/90 – π/18 radians<br><br>Steps: π/90 radians | 0 – π radians<br><br>Steps: π/4 radians | 0 – π radians<br><br>Steps: π/4 radians |

Figure 10 – Table 2

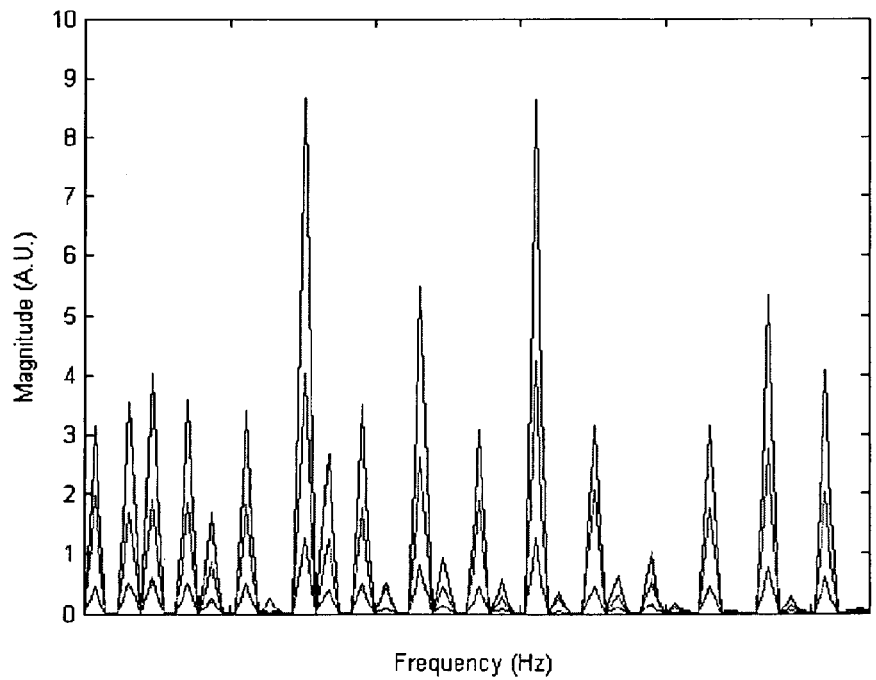

Figure 11

| Some Relevant Frequencies | Correlation |
|---|---|
| $\omega_1$ | 0.9969 |
| $\omega_2$ | 0.9981 |
| $\omega_3$ | 0.9987 |
| $2\omega_1$ | 0.9921 |
| $2\omega_2$ | 0.9863 |
| $2\omega_3$ | 0.9993 |
| $3\omega_1$ | 0.9989 |
| $3\omega_2$ | 0.9854 |
| $3\omega_3$ | 0.9836 |
| $5\omega_1$ | 0.9950 |
| $5\omega_2$ | 0.9920 |
| $\omega_1+\omega_2$ | 0.9829 |
| $\omega_1+\omega_3$ | 0.9845 |
| $\omega_2+\omega_3$ | 0.9947 |

Figure 12 – Table 3

| Latent Variables | SEC (mg/dL) | SEP (mg/dL) |
|---|---|---|
| 1 | 53.6655 | 28.3869 |
| 2 | 15.0378 | 15.0371 |
| 3 | 1.3198 | 3.0890 |
| 4 | 10.0577 | 9.6893 |
| 5 | 1.6343 | 0.4329 |

Figure 14 – Table 4

NON-INVASIVE POLARIMETRIC APPARATUS AND METHOD FOR ANALYTE SENSING IN BIREFRINGENT MEDIA

CROSS-REFERENCE TO RELATED APPLICATIONS AND STATEMENT REGARDING SPONSORED RESEARCH

The present invention claims the benefit of the PCT/US2008/082742 filed Nov. 7, 2008, which claims priority to the provisional patent application Ser. Nos. 61/002,195 filed Nov. 7, 2007, and 61/005,120 filed Dec. 3, 2007. This invention was not made with any government support and the government has no rights in this invention.

BACKGROUND OF THE INVENTION

Diabetes Mellitus is a common and serious chronic disease, which afflicts about 177 million people worldwide, 17 million people in the United States and is the fourth leading cause of death. It leads to long-term complications such as coronary artery disease, hypertension, retinopathy, neuropathy and nephropathy. Research indicates that self-monitoring of blood glucose levels prevents or slows down the development of these long term complications. An optical polarimetric glucose sensor provides a means for the noninvasive measurement of glucose concentration, thereby reducing pain and complications associated with the current invasive methods.

The use of polarimetry in the detection of analyte concentration has existed for several years. Pohjola demonstrated that glucose concentration in the aqueous humor of the eye is correlated to that of blood. In 1982, March et al. were the first to propose the use of polarimetry to indirectly estimate blood glucose levels via the aqueous humor of the eye. They found in order to measure millidegree sensitive rotations due to glucose at physiological levels a very sensitive and stable polarimeter is required. In the past decade, considerable work has been done in the development of such a polarimeter. Cote et al. reported on the potential for millidegree sensitivity by utilizing a true phase technique. This work was later followed by Cameron et al. who reported on a Faraday based polarimeter using a digital closed-loop feedback technique with sub-millidegree sensitivity. Since then, different polarimetric variations have been illustrated by several groups to measure glucose concentration. Chou et al. reported on a polarimeter utilizing an optical heterodyne approach with the ability to detect glucose levels below 10 mg/dl; however, the open loop system lacked stability due to fluctuations in the laser intensity and noise. Recently, Ansari et al. proposed a theoretical model using the Brewster's reflection off the eye lens for measuring glucose concentration.

Though aqueous humor of the eye contains glucose, it also has other optically active components that can contribute to the overall optical rotation. To estimate glucose concentration in the presence of other optically active components, King et al. demonstrated the use of a multi-spectral Pockels cell based system. This work was followed by Cameron et al. who used a multi-spectral Faraday-based system which also demonstrated the potential to overcome rotations due to the presence of other optically active components. Though glucose concentration in the aqueous humor correlates to that of blood, there is a transport time delay between the diffusion of glucose from the blood into the aqueous humor. If such measurements are to be of benefit to a diabetic person as a reliable predictor of blood glucose concentration, the time delay should be below 10 minutes. In 2001, Cameron et al. measured the transport time delay in a rabbit model and had shown this delay to be under the 10 minute threshold. Recently, Baba et al. have shown the effects of temperature and pH to be negligible in the normal physiological range.

The main problem currently hindering the development of a viable polarimetric system to indirectly measure blood glucose levels in the aqueous humor of the eye is the birefringence of the cornea associated with motion artifact. Since the birefringence of the cornea is spatially varying, as the cornea moves with respect to the sensing light beam, the motion induces time varying birefringence which tends to mask the detected glucose signal.

Time varying corneal birefringence due to motion artifact is the main factor limiting in vivo polarimetric glucose measurements in the eye which has not been addressed by current glucose sensing polarimeters, except for that disclosed by Cameron, the same inventor herein, U.S. Pat. No. 7,245,952, in which a noninvasive birefringence compensated glucose sensing polarimeter was disclosed that could compensate for time varying corneal birefringence. In this case, a propagated polarized laser beam, not backscattered, passes directly through the anterior chamber of the eye and does not interact with the lens or retina. In addition, the compensator is tied to an autonomous controller system to compensate for corneal birefringence effects in real-time. In other disclosed work, U.S. Pat. No. 5,303,709 disclosed a system to facilitate diagnosis of retinal eye disease. To minimize effects of corneal birefringence, this system utilized a backscattered beam from the retina coupled to a variable retarder to reduce corneal birefringence contributions on nerve fiber retinal layer measurements. The compensation implementation in the '709 patent incorporated a polarization sensitive confocal system integrated into a scanning laser retinal polarimeter.

U.S. Pat. No. 6,704,106 disclosed a method and system to cancel retardance error in regards to retinal nerve fiber layer measurements. To achieve this, four retardance measurements collected over one complete rotation of a mechanically rotated half-wave retarder are averaged to minimize effects of system birefringence, leaving a mean retardance measurement free of residual polarization bias.

In U.S. Pat. No. 6,356,036, a system and method for determining birefringence on the anterior segment (i.e., cornea and lens) of a patient's eye was disclosed. This method involved using a backscattered (i.e. reflected) light beam similar to that disclosed in '709 except the patient's lens reflection intensity through confocal imaging is no longer used as a reference and birefringence of all segments of the eye that are anterior to the retina are determined using a direct polarization beam. In other words, '036 eliminated the need for a confocal imaging system and the scanning laser polarimeter was now able to use the same path to measure birefringence of the anterior segment of the eye.

SUMMARY OF THE INVENTION

In one aspect, there is provided herein a noninvasive polarimetric apparatus used to measure levels of a substance in a sample that may be birefringent in nature in the presence of three dimensional motion comprising:

a polarization system configured to generate multiple states of polarized light wherein birefringence and retardance are introduced in the polarized light, and configured to at least partially interact with the sample with the birefringed/retarded polarized light, whereby a signal is generated, and an analyzer system configured to receive the a signal obtained by the sample generated by the birefringed/retarded polarized light and configured to analyze the state of polarization and determine optical rotation which is encoded in the detected signal.

In a particular aspect, there is provided herein a polarimeter where one or more of the polarization system and the analyzer system are configured to generate an oscillating birefringence contribution.

In another particular aspect, there is provided herein a polarimetric apparatus where one or more of the polarization system and the analyzer system comprise a variable retarder(s).

In another particular aspect, there is provided herein a polarimetric apparatus where one or more of the polarization system and the analyzer system comprise one or more variable retardance based modulator systems.

In another particular aspect, there is provided herein a polarimetric apparatus where the polarization system comprises a first variable retardance modulator, a second variable retardance modulator, and a third variable retardance modulator, and the analyzer system comprises a fourth variable retardance modulator, a fifth variable retardance modulator, and a sixth variable retardance modulator.

In another particular aspect, there is provided herein a polarimetric apparatus where the polarization system comprises:

a first modulator having its fast axis oriented at an angle of −45° with respect to the vertical position, a second modulator having its fast axis oriented at 45° with respect to the vertical position, and a third modulator having its fast axis oriented at an angle of 0° with respect to the vertical position;

and, wherein the analyzer system comprises:

a fourth modulator having its fast axis oriented at an angle of 0° with respect to the vertical position, and a fifth modulator having its fast axis oriented at 45° with respect to the vertical position, and a sixth modulator having its fast axis oriented at an angle of −45° with respect to the vertical position;

In another particular aspect, there is provided herein a polarimetric apparatus where the polarization system comprises:

a first modulator having its fast axis oriented at a 1st angle with respect to a vertical position, a second modulator having its fast axis oriented at a 2nd angle with respect to the first modulator, and a third modulator having its fast axis oriented at a 3rd angle with respect to the second modulator;

and, wherein the analyzer system comprises:

a fourth modulator having its fast axis oriented at 4th angle with respect to a vertical position, a fifth modulator having its fast axis oriented at a 5th angle with respect to the fourth modulator, and a sixth modulator having its fast axis oriented at a 6th angle with respect to the fifth modulator;

Various objects and advantages of this invention will become apparent to those skilled in the art from the following detailed description of the preferred embodiments, when read in light of the accompanying drawings.

BRIEF DESCRIPTION OF THE DRAWINGS

FIG. 1a is a schematic illustration where the variable retarder(s) cause the x-component of the electric field to lead the y-component.

FIG. 1b is a schematic illustration where the variable retarder(s) cause the x-component of the electric field to lag the y-component FIG. 1c is a schematic illustration where the variable retarder(s) cause the x and y-components of the electric field to be in phase

FIG. 7 contains Table 1, showing the polarizing components and their Mueller matrices.

FIG. 9a shows the detected amplitude versus posterior corneal birefringence for a fixed glucose concentration without compensation.

FIG. 9b shows a glucose calibration plot for an uncompensated data set.

FIG. 10 is Table 2 showing the different optical parameters varied during the simulation.

FIG. 11 is a FFT showing magnitude versus frequency for a glucose concentration of 300 mg/dl for three different sets of retardances and azimuthal angles.

FIG. 12 is Table 3 which shows a list of correlation coefficients at certain relevant frequencies.

FIG. 13a shows the actual vs. predicted glucose concentration for calibration.

FIG. 13b shows the actual vs. predicted glucose concentration for validation.

FIG. 14 is Table 4 which shows the SEC and SEP for a different number of latent variables in the formation of respective calibration models.

DETAILED DESCRIPTION OF THE PREFERRED EMBODIMENT(S)

Figure 1A:
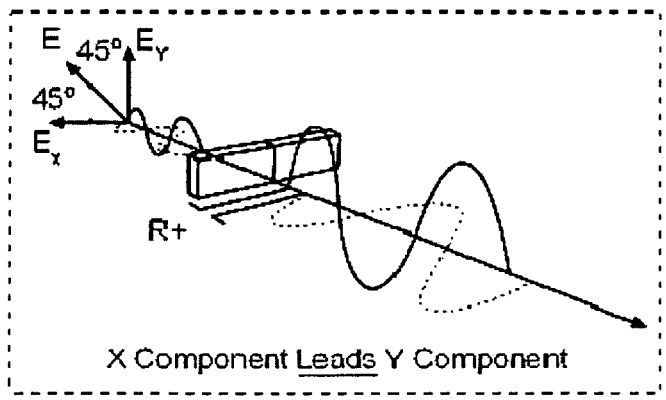
FIGS. 1a, 1b and 1c show the possible effects of a variable retarder(s) on the polarization state of light.

In one aspect, there is provided a system to sense glucose concentration in the presence of corneal birefringence is disclosed.

In a particular aspect, the system employs a polarimetric based design which incorporates six modulated variable retarders capable of generating and analyzing all states of polarization. The system quantitates optical rotation in a complex dynamically changing birefringent media.

In another aspect, there is provided a system to measure glucose in the presence of birefringence using a partial least squares (PLS) based method for calibration.

The system described herein has significant advantages over previously reported approaches, including, but not limited to the ability to sense glucose concentration in the presence of time-varying anterior and posterior sample birefringence, independence of rotational changes in the fast/slow axes of the birefringent sample, and direct glucose calibration without knowing the sample birefringence.

In a particular aspect, the system provides for the ability to sense glucose concentration in the presence of time-varying anterior and posterior sample birefringence. In addition, the system is independent of rotational changes in the sample's fast/slow axes. Further, the system allows for direct glucose calibration without knowing the birefringence of the sample being tested.

The polarimetric system incorporates six modulators and is not limited to linear polarization. The polarimetric system can generate and analyze all states of polarization, including circular, elliptical and linear polarization states.

The present polarimetric system incorporates multivariate partial least squares (PLS) linear regression for calibration rather than using the standard least squares approach commonly used in most polarimetric approaches.

In a particular aspect, the system uses optical polarimetry to detect small millidegree changes in rotation of the glucose sample by passing a beam of light through the sample. The intensity of the transmitted light measured with a photodetector throughout the optical train will be related to the amount of rotation in polarization due to the glucose sample, thus related to the sample's concentration.

In the present system, optical polarimetry is applied in the development of a non-invasive sensor for birefringent media, which contains, but not limited to glucose. For ease of illustration herein, such birefringent media will generally be referred to as comprising glucose, but it should be understood that the present system can be used with many other types of birefringent and optically active media.

As such, in a particular aspect, in order to use polarimetry for in vivo glucose detection, a suitable sensing site is chosen. Several tissues in the body, such as the skin, are extremely scattering in nature. This scattering effect tends to significantly depolarize the light making it difficult to measure the small rotations due to physiological glucose levels (i.e., low signal to noise ratio) and the scattering events in themselves also affect the overall state of polarization. As such, polarimetric detection through the skin is a very difficult task; however, the body does possess a sensing site that is well suited for optical polarimetry as well as other sensing modalities. The eye is unique in that the cornea provides a low scattering window into the body. The fluid contained in the anterior chamber, known as the aqueous humor, is also relatively scattering free.

An important task of in vivo polarimetric glucose sensing is to find an appropriate way to optically access the aqueous humor of the human eye. While optical polarimetry has contributed in the quantification of pure cane sugar for several years, it has not been until recently that the sensitivity of optical polarimeters has increased to facilitate measurement of physiological glucose concentrations.

It was first demonstrated by Pohjola that glucose concentration in the aqueous humor is correlated to that of blood. Measurement of millidegree rotations due to low glucose concentrations seen in physiological conditions requires a stable and sensitive polarimeter. In 1982, March et al. were the first to propose the use of polarimetry to indirectly estimate the blood glucose levels via the aqueous humor of the eye. Several research groups since have made considerable advances in the development of such a polarimeter. Coté et al. reported on the potential of millidegree sensitivity by utilizing a true phase technique. This work was further improved by Cameron et al. who reported on a Faraday based polarimeter with digital closed-loop feedback technique with sub-millidegree sensitivity. This technique also increased the repeatability and stability of optical polarimetric measurements. Chou et al. showed experiments utilizing an optical heterodyne technique, substantiating the correlation between blood glucose and the aqueous humor glucose. Chou et al. showed that the total rotation contributed by the analyzer, cornea and aqueous glucose was less than 2.5° in the measuring range of 50-400 mg/dl.

Another problem encountered when using the aqueous humor of the eye as the sensing site is the contribution of other optically active molecules in masking the optical rotation due to glucose alone. King et al. demonstrated the use of a multi-spectral Pockels cell based system in order to estimate glucose concentration in the presence of other optically active components. Cameron et al. later used a multi-spectral Faraday-based system that demonstrated the potential to overcome rotations due to the presence of other optically active molecules commonly found in the aqueous humor.

Another problem associated with using polarimetry for blood glucose measurement is the potential lag time between blood and aqueous humor glucose concentrations during periods of rapidly shifting blood glucose concentrations. For reliable measurements of blood glucose concentration using aqueous humor as the sensing medium, the time delay should be less than 10 minutes. In 2001, Cameron et al. measured transport time delay in a rabbit model to be under this threshold of 10 minutes. Most recently, the effect of temperature and pH on polarimetric based glucose measurements, with the eye as the proposed sensing site, has been demonstrated by Baba et al.

Birefringence coupled with motion artifact is another problem currently hindering noninvasive optical polarimetry with using the eye as the sensing site. Cameron reported on the development of a polarimetric-based instrument and method in U.S. Pat. No. 7,245,952 which was further improved (Cameron and Anumula, Diabetes Technology & Therapeutics, 8(2), pp. 156-164, 2006) in which a compensation approach enabled physiological glucose measurements to be acquired in birefringent media. This approach performed ideally for fixed rotational angle corneal retardance, however, in practice the birefringence angle constantly varies in the presence of motion artifact. Therefore, this approach has limitations in its ability to precisely quantify glucose in the presence of motion artifact, especially with three dimensional motion artifacts.

Thus, the present system described herein provides a robust system to measure glucose concentrations accurately without being affected by corneal birefringence and motion artifacts.

The invention will now be illustrated by the following non-limiting examples.

EXAMPLES

Variable Retarders

Figure 1B:
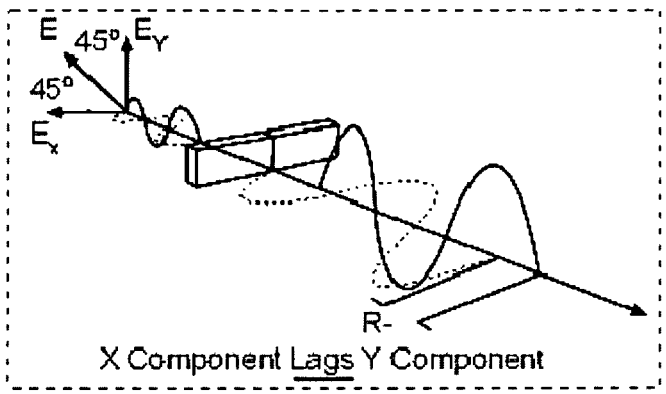
Figure 1C:
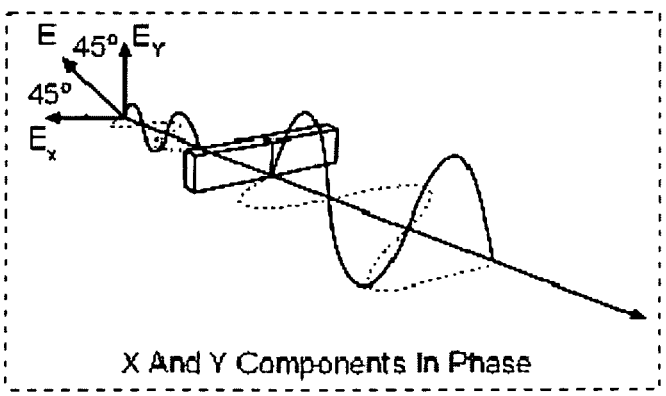

Retarders are optical elements that can introduce a set phase delay between two orthogonal states of polarized light. There can be different ways of achieving the phase delay. There are fixed wave plates that are wavelength dependent that can provide a set phase shift. For example, quarter wave plates can create circular as well as elliptical polarized light from linearly polarized light and half wave plates can rotate linear polarized light to its orthogonal state. The phase delay relationship between orthogonal states of an electric field and its polarization state are illustrated in FIG. 1.

Variable retarders, unlike fixed wave plates, are capable of introducing an arbitrary controlled phase shift between two orthogonal states of polarized light. This arbitrary phase shift can be produced in many different ways. Variable retarders, currently available, use different principles and technology such as the Pockels Effect, Photoelastic Effect, Kerr Effect, Faraday Effect and even liquid crystal technology to produce a variable phase shift. In the examples described herein, although all the above technologies are viable, the Photo Elastic Modulator (PEM) technique is well suited for its implementation.

In one particular embodiment of the present system, six variable retarders, modulated at unique and distinct frequencies are used, three each on the anterior and posterior side of the cornea or sample, respectively. The arrangement of the optical fast/slow axes of the three modulators at the anterior side of the sample or cornea with respect to each other is demonstrated in FIG. 2.

In one embodiment, the first modulator (VRM1) has its fast axis at an angle of −45° with respect to the vertical position. The second modulator (VRM2) has its fast axis oriented at 45° with respect to the vertical position. The third modulator (VRM3) has its fast axis oriented at an angle of 0° with respect to the vertical position. The same arrangement in reverse order is used in the analyzer portion of the designed system located after the posterior side of the sample or cornea.

Figure 3:
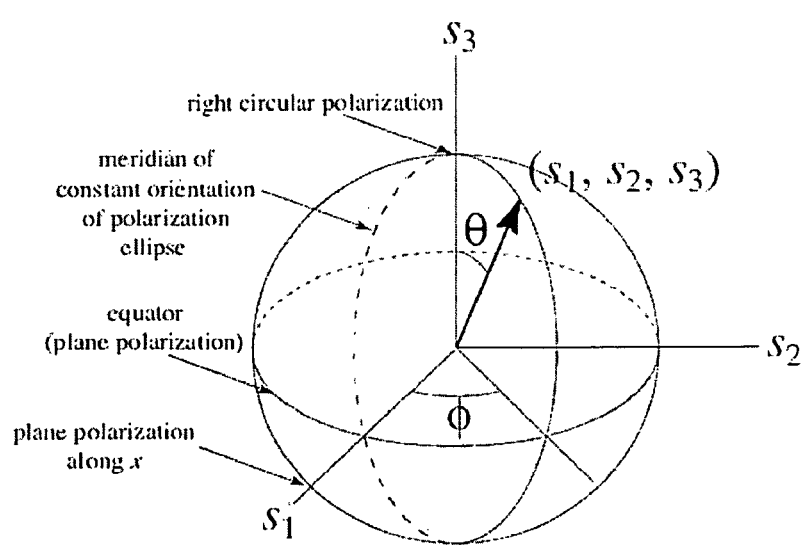
FIG. 3 is a schematic illustration of a Poincarè sphere.

The polarization state of the incoming light entering the sample is modulated through the use of the three initial variable retarders. The result is light which oscillates between left and right circularly polarized light, with elliptically polarized light states between these extremes. Continuously changing the retardance of each variable retarder, each at a respective frequency $\omega_1$, $\omega_2$ and $\omega_3$, produces continuously changing polarization states in the light interacting with the sample. These varying polarized states of light can be illustrated as different location on the surface of a Poincarè sphere as shown in FIG. 3.

Poincarè Sphere Representation

The Poincarè Sphere is used to describe the polarization and changes in polarization of an electromagnetic wave. The Poincarè sphere displays the three independent Stokes parameters S1, S2, S3 as points on, or inside, a sphere, as shown in FIG. 3.

The Poincarè sphere representation, in which the point (S1, S2, S3), which describes the state of polarization, lies at a distance P from the center of the sphere. The normalized Poincarè sphere, uses the normalized Stokes parameters (for P>0), where $s_1=S_1/PS_0$, $s_2=S_2/PS_0$, $s_3=S_3/PS_0$.

The point (s1, s2, s3) lies on the surface of a sphere with radius 1, since $s_1^2+s_2^2+s_1^2=1$. In effect, this illustrates the state of polarization of the polarized part of the beam.

Each point location on the sphere's surface corresponds to a unique state of polarization: the north and south poles are the states of circular polarization and points along the equator correspond to different states of linear polarization. Points on the northern and southern hemispheres correspond to elliptically polarized light of different handedness.

In the examples presented herein, the three initial modulators are set up in such a way that the entire surface of the Poincarè will be traversed given a sufficient time period.

Figure 4:
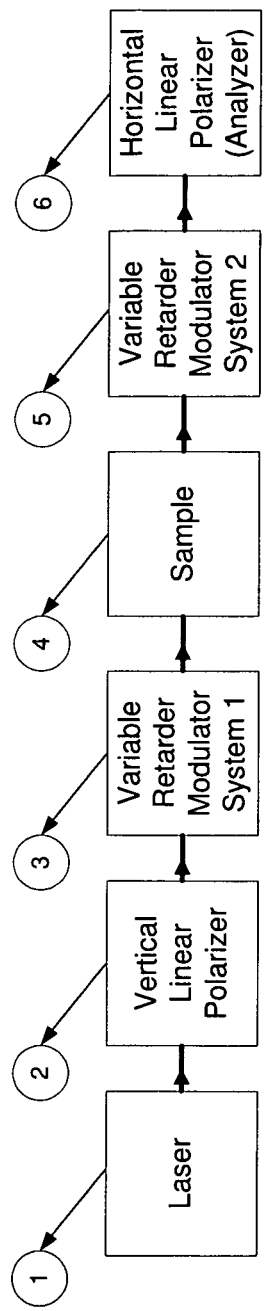
FIG. 4 shows a generalized block diagram of the polarimeter

Generalized Model of the Robust Non-Invasive Polarimetric Apparatus and Method for Analyte Sensing in Birefringent Media FIG. 4 shows the generalized block diagram of the designed sensing polarimeter capable of measuring analyte concentrations in a birefringent sample. An unpolarized laser source 1 is used as the input. This laser light is then polarized by a linear polarizer 2 with its transmission axis oriented in the vertical direction. Three variable retarder based modulators 3 provide modulation of the polarization state of the incoming light as previously described.

Figure 2:
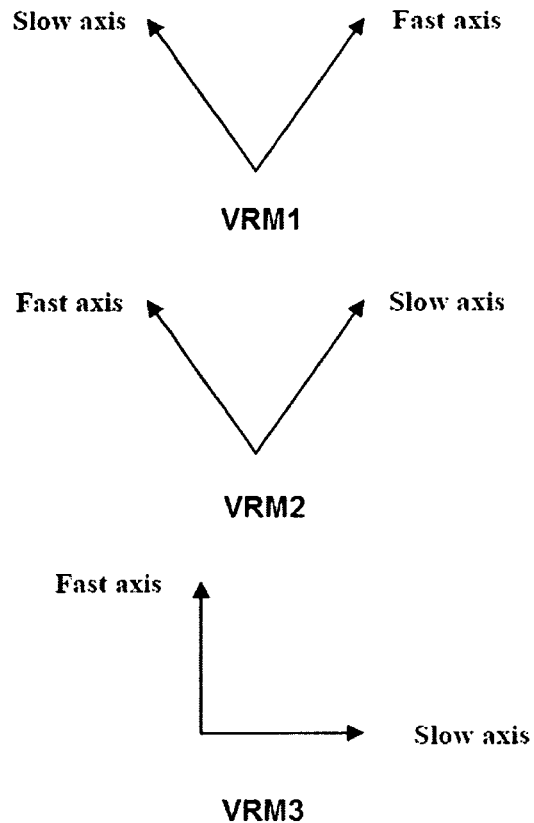
FIG. 2 is a schematic illustration showing the arrangement of 3 variable retarder's with respect to each other.

The arrangement of the three modulator system is shown in FIG. 2. The light then encounters the birefringent sample, 4, containing glucose that induces optical rotation in the polarization state of incoming light. After the sample, three additional polarization modulators 5 are arranged in the reverse order at the analyzer end of the system. The system is terminated with another linear polarizer 6 with its transmission axis oriented in the horizontal direction. Its purpose is to transform changes in the electric field into detectable intensity changes that can be measured with a light detector. To more fully understand the operation of the system, it is important to understand the complexity sample 4 (i.e. the eye/cornea model) that contains the glucose sample.

Eye Simulation Model

In order to simulate the eye/cornea, two important aspects of corneal behavior must be considered, (1) anterior and posterior birefringence and (2) motion induced changes. The cornea is not a stable birefringent element such as a fixed wave plate; motion artifact can induce dynamically changing birefringence contributions, as the cornea is spatially birefringent. These changes will tend to mask the glucose signature which is the desired measurement or variable of interest. In addition, the fast and slow axes for both the anterior and posterior corneal surfaces may also undergo rotational changes due to motion artifact(s).

Figure 5:
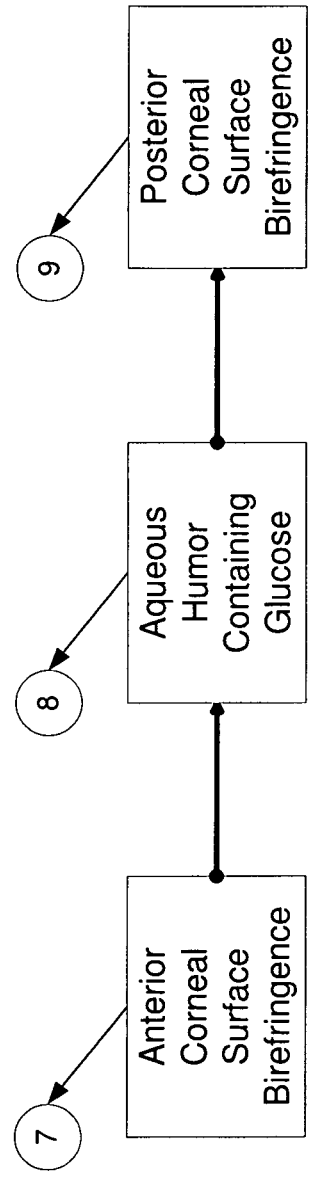
FIG. 5 shows a generalized block diagram of the cornea/eye sample model.

A straight path through the anterior chamber of the eye has several advantages. One significant advantage is that the light does not come in contact with the retina, thus minimizing the possibility of light related retinal effects. Several methods have been reported on to couple light through the anterior chamber of the eye. In 1999, Cameron et al. (Diabetes Technology & Therapeutics, vol. 1, pp. 135-143, 1999) performed in vivo experiments on New Zealand rabbits and demonstrated a technique which permits laser light to be transmitted using a straight path through the anterior chamber of the eye. A schematic block diagram of the cornea/eye sample model used in the approach and simulations presented herein is shown in FIG. 5.

A straight light path through the eye includes the anterior corneal surface 7 which introduces a birefringence contribution associated with a respective angular rotation of its preferred fast/slow axis. The light then enters the anterior chamber of the eye with an approximate path length of 1 cm. As the light propagates through the aqueous humor 8 contained within the anterior chamber, optical rotation due to glucose and/or other components is introduced. The light then reaches the posterior corneal surface 9 where an additional birefringence contribution is introduced along with another respective angular rotation associated with the preferred fast/slow axis.

Figure 6:
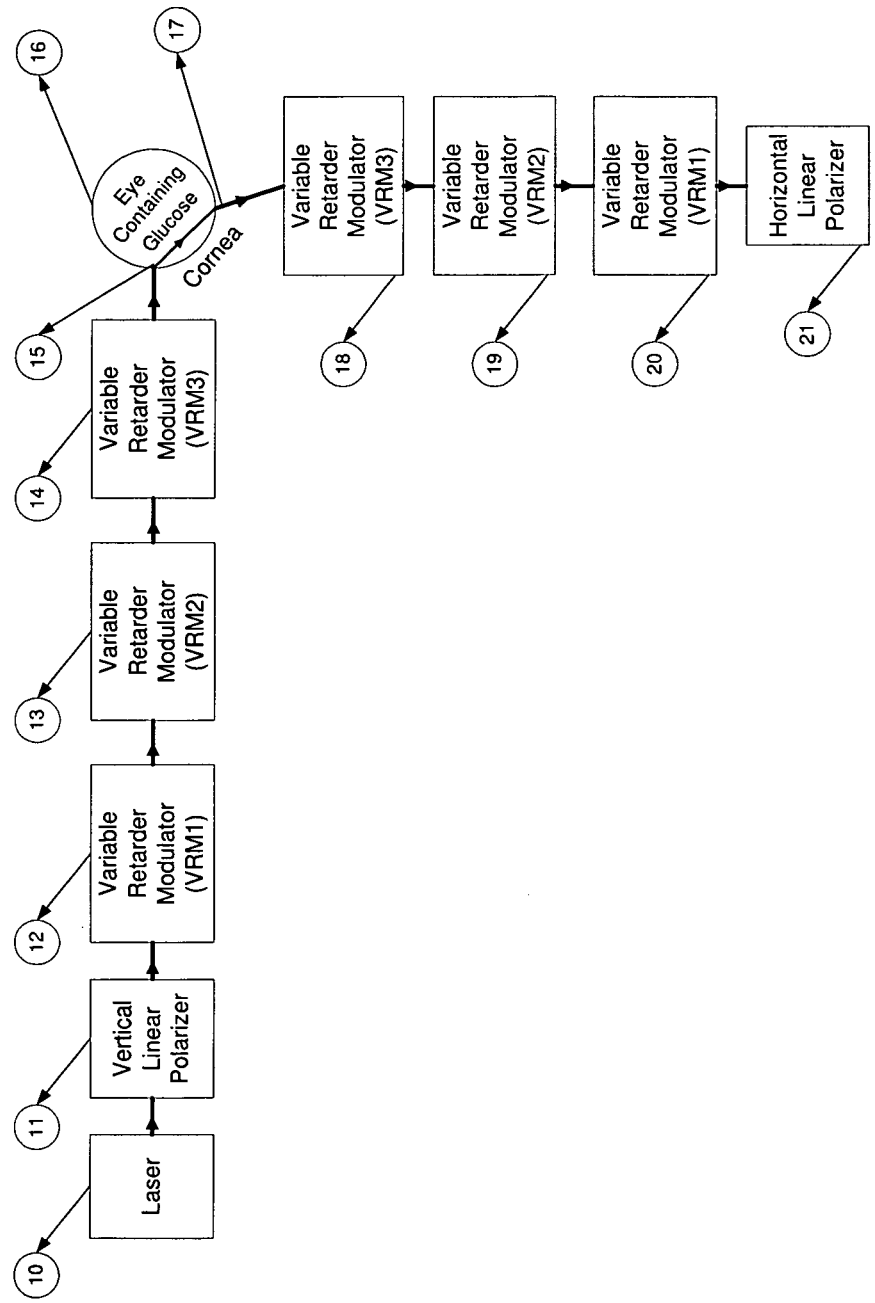
FIG. 6 shows a detailed block diagram of the designed polarimeter.

In the model used for the examples described herein, variable retarders are used to simulate birefringence due to both the anterior (AR) and posterior (PR) corneal surfaces of the eye. The variable retarder induces variable phase retardances ($\delta_A$ for the AR and $\delta_P$ for the PR) and variable azimuthal angles ($\phi_A$ for the AR and $\phi_P$ for the PR). These dynamically changing parameters in essence cause the linear polarized light beam to become elliptical in nature, thus tending to mask the signature of glucose. As depicted in FIG. 6, as the light generated by the laser 10 passes through the initial polarizer 11, the phase shifts introduced by each modulator (VRM1 (12), VRM2(13), and VRM3(14)) continuously change resulting in unique polarization states that then interact with the cornea/glucose/cornea (15, 16, 17) sample. Depending on the degree and characteristics of the corneal birefringence, a signal representative to the glucose concentration will be generated for each respective input polarization state. A secondary signal is then produced as the light exits the eye and passes through the respective analyzer optics (VRM3(18), VRM2(19), VRM3(20) and the horizontal linear polarizer (21)) which is detected as a complex time varying light intensity signal. Spectral information resulting from the unique modulation frequencies of each system modulator as well as due to the interaction with the sample are revealed through the processing of the detected time based signal with a Fast-Fourier Transform algorithm. The cumulative data set for different sample glucose concentrations and birefringence characteristics is then processed through a technique based off the partial least squares (PLS) method to determine a calibration model for estimation of the glucose concentration in unknown samples.

The described system herein is modeled using the Stokes vector/Mueller matrix theory and is explained in detail below.

Stokes/Mueller Simulation Model of the Robust Non-Invasive Polarimetric Apparatus and Method for Analyte Sensing in Birefringent Media A detailed block diagram of the designed sensing polarimeter capable of measuring analyte concentrations in a birefringent sample is shown in FIG. 6. The components present in this optical train are the laser 10, polarizer 11, three variable retardance based modulators 12, 13, and 14, a variable retarder 15 due to the anterior corneal surface, glucose sample 16, a variable posterior retarder 17 representing the posterial corneal surface, three variable retardance based modulators 18, 29, and 20 and a linear polarizer 21 which collectively serve as the analyzer. The use of the Stokes vector/Mueller matrix theory is an efficient method to model the system to calculate the intensity based output light signal. The Mueller matrices for the different polarizing components are presented in FIG. 7-Table 1.

The Stokes vector/Mueller matrix representation of the designed system is given by equation:

$$[I,Q,U,V]^T = (HA)(VRM1)(VRM2)(VRM3)(PR)(S)(AR)(VRM3)(VRM2)(VRM3)(VP)(L)$$

Here, the system of matrices is represented in the order opposite to the propagation of light. In regards to the respective matrix elements, $\phi_A$ is the arbitrary fast-axis orientation measured from the horizontal and $\delta_A$ is the retardance due to the anterior corneal retarder. Similarly, $\phi_P$ and $\delta_P$ are the angle and retardance due to the posterior corneal retarder. The optical rotation due to the glucose sample is $\phi_g$. The modulation frequencies for the variable retarder modulators are $\omega_1$, $\omega_2$ and $\omega_3$, respectively. The arbitrary fast-axis orientation for each modulator measured from the horizontal are, $\phi_1$, $\phi_2$, and $\phi_3$ respectively. For each modulator, the time-dependent phase shift or retardance is given by: $\delta(t) = M(\lambda)\sin(\omega t)$, where $M(\lambda)$ is the amplitude modulation at a specific wavelength ($\lambda$) of light and $\omega$ is the respective modulation frequency.

Noninvasive Glucose Sensing Polarimeter Simulations

The designed glucose sensing polarimeter as explained herein was simulated using MATLAB®. In an initial simulation, fixed azimuthal angles ($\phi_A$, $\phi_P$) and fixed retardances ($\delta_A$, $\delta_P$) for both the anterior and posterior corneal retarders were used.

This implies that no change in sample birefringence or rotational axes was introduced in the simulated model. Glucose concentrations from 100-5000 mg/dl in increments of 100 mg/dl were employed in the simulation. The modulation frequencies of the respective modulators used were $\omega_1$, $\omega_2$ and $\omega_3$, respectively. The output of interest from the simulation is the detected intensity. The raw detected time based intensity signal detected for each glucose concentration was processed using a Fast Fourier Transform (FFT) algorithm.

Figure 8A:
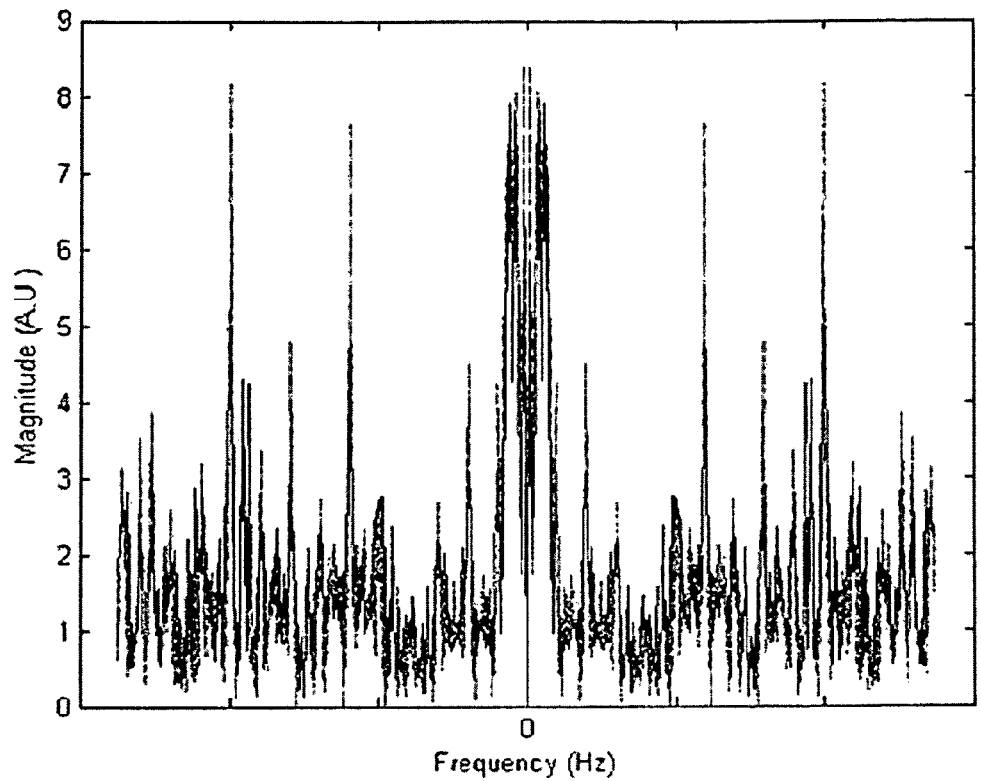
FIG. 8a shows the FFT spectrum showing magnitude versus frequency plot.
Figure 8B:
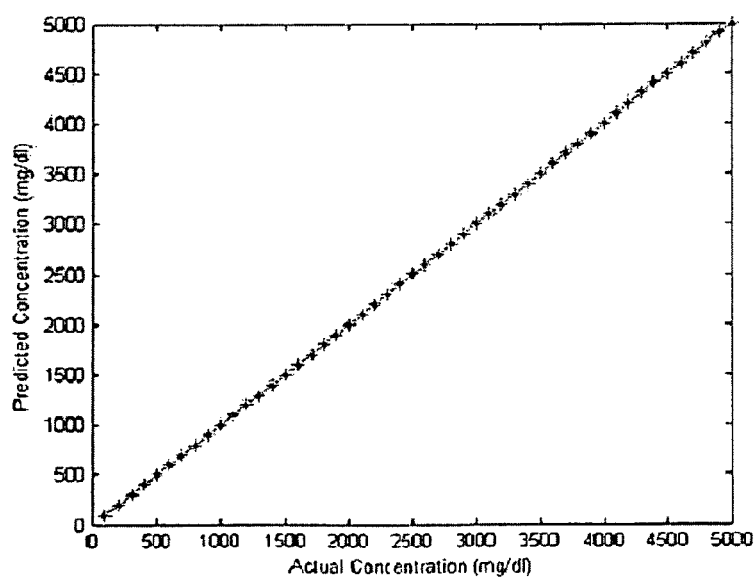
FIG. 8b shows the actual versus predicted concentration for the ideal system.

The overlapping spectral responses are shown in FIG. 8a. The FFT operates on blocks of samples at a time and is used to analyze the spectral frequency content of the output light beam. The cumulative data set, outputted from the FFT, for all glucose concentrations was used to formulate a calibration model using the Partial Least Squares (PLS) technique. The resulting model was then used to re-predict the respective glucose concentration levels as shown in FIG. 8b.

Polarimetric Calibration Using Partial Least Squares (PLS)

The general purpose of multiple regression is to determine or represent the relationships between several independent or predictor variables and a dependent or criterion variable. The general task in multiple linear regression analysis is to fit a straight line to a number of points. Partial least squares regression is an extension of the multiple linear regression. In its most general form, a linear model specifies the (linear) relationship between a dependent (measured or registered) variable Y, and a set of predictor variables, the X's, so that $$Y = b_0 + b_1 X_1 + b_2 X_2 + \ldots + b_P X_P$$

In this equation, $b_0$ is the regression coefficient for the intercept and the $b_i$ (i=1–p) values are the regression coefficients (for variables 1 through p) computed from the data.

Multiple linear regression modeling can be extended in a number of ways to focus on more complex data analysis problems. A multiple linear regression model serves as the basis for a number of multivariate methods such as discriminant analysis, principal components regression, and/or canonical correlations. Regardless, however, these multivariate methods all have two important characteristics in common. First, the methods impose limitations such that factors underlying the Y and X variables are extracted from the Y'Y and X'X matrices, respectively, and never from cross-product matrices involving both the Y and X variables. Secondly, the number of prediction functions can never surpass the minimum of the number of Y variables and X variables.

Partial least squares regression extends multiple linear regression without imposing the limitations employed by other techniques. In partial least squares regression, predictive functions are characterized by factors extracted from the Y'XX'Y matrix. The number of such prediction functions that can be extracted typically will surpass the maximum of the number of Y and X variables.

Partial least squares regression is therefore among the least restrictive of the various multivariate extensions of the multiple linear regression model. This flexibility allows it to be used in situations where conventional multivariate methods are severely limited, such as when there are fewer observations than predictor variables.

In at least one example, the plot (FIG. 8b) depicting the actual versus predicted glucose concentrations was generated using the PLS calibration method.

Effect of Birefringence on Polarimetric Glucose Sensing

Figure 9A:
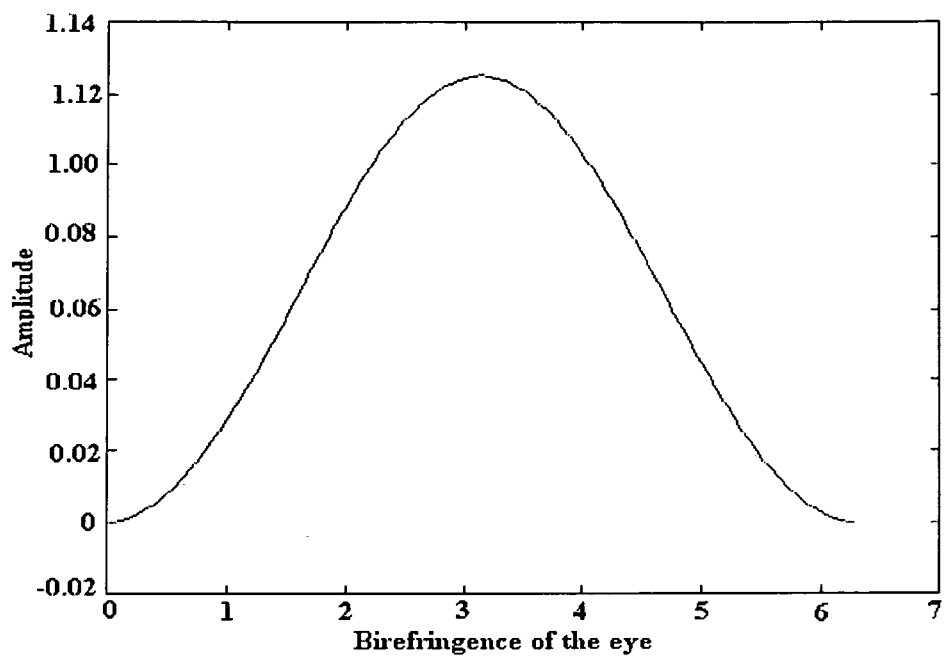
FIGS. 9a and 9b are graphs illustrating the effect of birefringence.
Figure 9B:
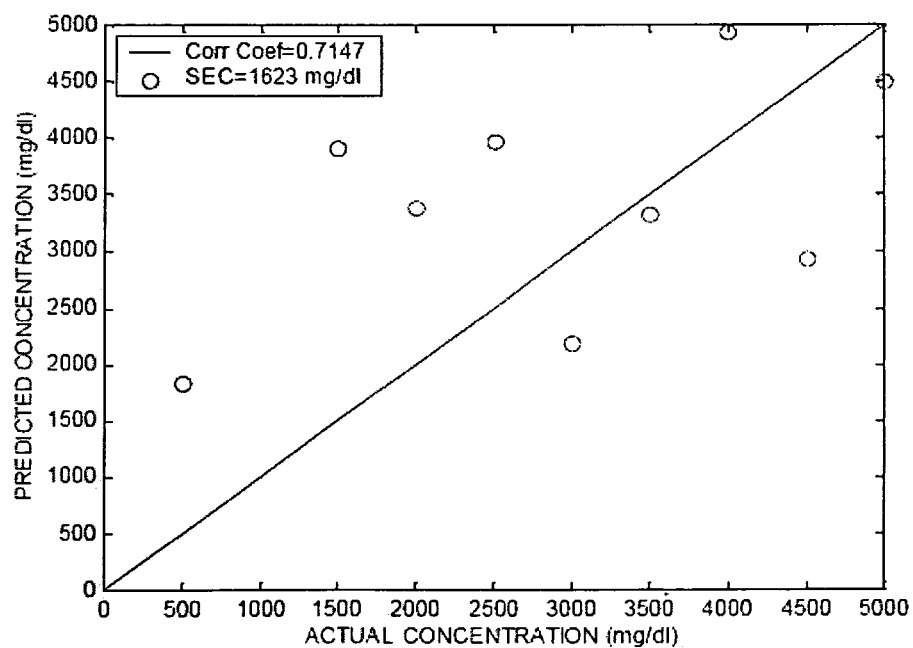

In U.S. Pat. No. 7,245,952 a theoretical model of a designed glucose sensing polarimeter was previously reported and used to illustrate the effect of birefringence on glucose detection. This system was evaluated without compensating for birefringence with glucose concentration fixed at 500 mg/dl as retardance was varied from 0-2π in steps of 0.01. As can be seen in FIG. 9a, the detected signal varies with the birefringence which masks the glucose signature (in the ideal case for no corneal birefringence, the curve should be constant for a fixed glucose concentration). Further demonstration of calibration and prediction of glucose concentration in an uncompensated system is shown in FIG. 9b. As can be seen, corneal birefringence effects have a significant impact on the accurate prediction of glucose concentration.

In the examples described herein, the proposed glucose sensing polarimeter has been designed to accurately measure glucose concentration in the presence of corneal birefringence.

Simulated Eye Phantoms

The simulations of the proposed system as explained herein were executed with varying retardances and azimuthal angles using the eye model depicted in FIG. 5. These parameters are summarized in FIG. 10 Table 2. The azimuthal angles ($\phi_A$, $\phi_P$) were varied from $\pi/90$-$\pi/18$ radians in increments of $\pi/90$ radians. The retardances ($\delta_A$, $\delta_P$) were varied from 0-$\pi$ radians in increments of $\pi/4$ radians. This simulation was performed with glucose concentrations ranging from 100-550 mg/dl in steps of 50 mg/dl. Each glucose concentration was held constant for all combinations of the four varying parameters $\phi_A$, $\phi_P$, $\delta_A$, and $\delta_P$.

Polarimetric Simulations

The final simulations were conducted using the theoretical model of the proposed polarimeter illustrated in FIG. 6 and the previously discussed simulated eye phantoms. Both glucose prediction in calibration and validation were performed using the computed PLS model. Of the cumulative data set collected for all eye phantoms, calibration data utilized 70% of this data set and 30% of the data set was used for independent validation of the calibration model.

The output signal for each sample corresponding to a unique concentration of glucose was processed via the Fast Fourier Transform prior to performing calibration with the PLS technique. As explained herein, the PLS technique was employed to determine a glucose calibration model which facilitated prediction of glucose concentrations. The standard error of calibration (SEC) and the standard error of prediction (SEP) were also computed.

For the PLS calibration, the use of five latent variables provided optimal performance. One possible explanation for optimal performance using five latent variables is that five different parameters were varied during the simulation; azimuthal angle and retardances for both the anterior and posterior corneal retarders, respectively, in addition to the varied glucose concentration. The FFT analysis of the raw data resulted in a complex spectrum with real and imaginary terms. In order to facilitate the understanding of the FFT spectrum, the magnitude versus frequency plot for glucose concentration of 300 mg/dl with three different sets of retardances and azimuthal angles were generated and shown in FIG. 11.

Figure 13A:
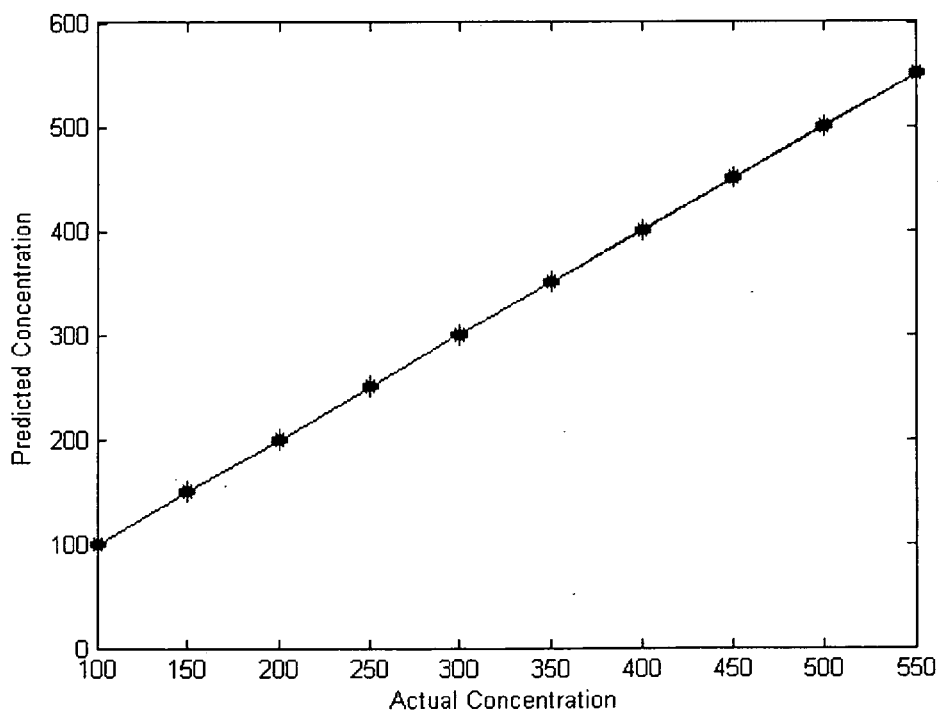
FIGS. 13a and 13b are graphs that show glucose prediction in the presence of sample birefringence (parameters varied indicated in FIG. 10).
Figure 13B:
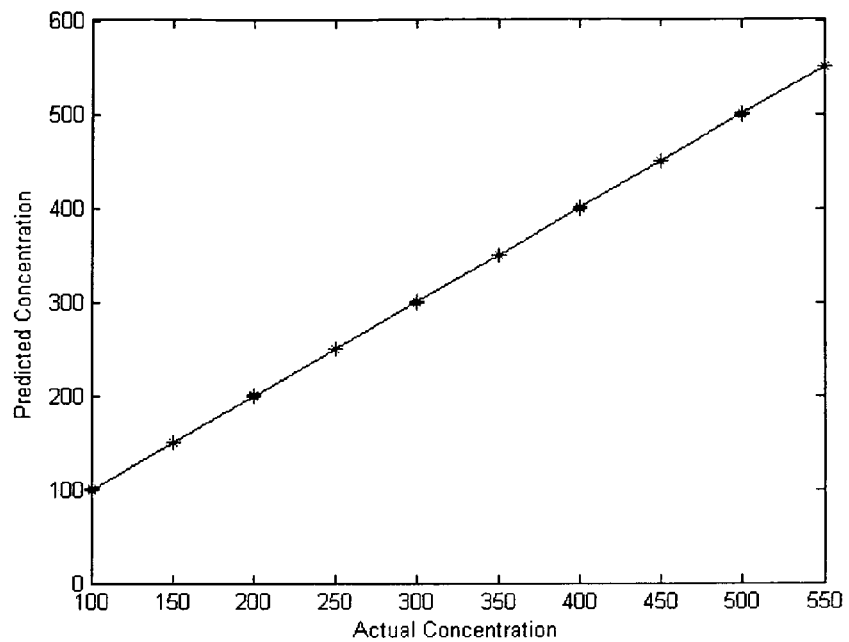

For reference purposes, after performing the FFT algorithm, correlation coefficients were computed for some relevant frequencies observed in the magnitude response (see Table 3 in FIG. 12). As can be seen, certain frequencies related to the modulation frequencies ($\omega_1$, $\omega_2$ and $\omega_3$) of the modulators VRM1, VRM2, and VRM3, respectively, possess very high correlation coefficients. The glucose prediction plots for samples containing varying corneal birefringence and glucose concentration (see FIG. 10 Table 2) for both calibration and validation experiments are shown in FIG. 13. These plots utilized a PLS calibration model formed with 5 latent variables. FIG. 13a shows the actual versus predicted concentration for calibration and FIG. 13b shows the actual versus predicted concentration plot for validation. In validation, an independent data set not included during the formation of the calibration model was utilized. As can be seen from the plots, each data set possesses a high degree of linearity.

For reference, the SEC and SEP for calibration models formed with different numbers of latent variables is shown in FIG. 14-Table 4.

Method for Non-Invasive Glucose Sensing Using Optical Polarimetry

In a particular aspect, there is provided herein a robust analyte sensing polarimeter which is capable of measuring physiological glucose concentrations in the presence of dynamically changing birefringence which involves the application of polarized light and utilizes the eye as the sensing site.

The polarimeter provides a non-invasive glucose sensing polarimeter that overcomes the problems associated with birefringence due to the cornea coupled to motion artifacts in the eye.

In the system described herein, variable retardance modulation is introduced prior to and after the eye based sample in order to overcome the effects of corneal birefringence. The present system utilizes 6 variable retardance modulators in the generation of the detected signal. The glucose concentration is predicted or measured using the PLS technique.

In yet another aspect, the system can include varying the retardance by smaller degrees and/or for a large number of glucose concentrations.

In still another aspect, the system can use different approaches to PLS regression for the prediction of glucose concentration.

Additional Examples of Birefringent Media and Uses Therefore

In another particular aspect, there is provided herein a polarimetric apparatus where the light generated has peak retardation that corresponds to a quarter of the wavelength of the light being used.

In another particular aspect, there is provided herein a polarimetric apparatus where the polarized light oscillates between left and right circularly polarized light, with elliptically polarized light occurring between the left and right circularly polarized light states.

In another particular aspect, there is provided herein a polarimetric apparatus where the frequency of polarization modulation is at the modulator frequency ($\omega_1$).

In another particular aspect, there is provided herein a polarimetric apparatus where magnitude and direction of the induced birefringence determines the polarization state of the light exiting the polarization apparatus.

In another particular aspect, there is provided herein a polarimetric apparatus where the polarization system is configured to continuously change the retardance of the polarized light, thus producing continuously changing polarization states.

In another particular aspect, there is provided herein a polarimetric apparatus where a noninvasive polarimetric apparatus is used to measure levels of a substance in a sample, that may be birefringent in nature, in the presence of three dimensional motion comprising:

at least one light source, at least one vertical polarizer, a polarization system configured to generate states of polarized light wherein birefringence and retardance are introduced in the polarized light, and configured to at least partially interact with the sample with the retarded polarized light, whereby a signal is generated, an analyzer system configured to receive the a signal obtained by the sample generated by the retarded polarized light and configured to measure levels of a substance in a sample in the presence of three-dimensional rotational sample movement, and at least one horizontal polarizer.

In another particular aspect, there is provided herein a polarimetric apparatus where the polarimetric apparatus is configured to apply a partial least square (PLS) analysis to the signal or post-processed signal.

In another particular aspect, there is provided herein a polarimetric apparatus where the system is configured to extract one or more generated frequencies that combine predictive information from the sample.

In another particular aspect, there is provided herein a polarimetric apparatus where the analyzer system is configured to receive the signal from the sample in an at least partially transmissive mode.

In another particular aspect, there is provided herein a polarimetric apparatus where the analyzer system is configured to receive the signal from the sample in an at least partially reflectance mode.

In another particular aspect, there is provided herein a polarimetric apparatus where the analyzer system is configured to receive the signal from the sample in an at least partially absorptive mode.

In another particular aspect, there is provided herein a polarimetric apparatus where the substance in the sample is an optically active substance.

In another particular aspect, there is provided herein a polarimetric apparatus where the substance in the sample causes a change in refractive index to be measured in the sample.

In another particular aspect, there is provided herein a polarimetric apparatus where the substance in the sample causes absorption data to be measured in the substance.

In another particular aspect, there is provided herein a polarimetric apparatus where the sample comprises a birefringent medium.

In another particular aspect, there is provided herein a polarimetric apparatus where the sample is substantially transparent.

In another particular aspect, there is provided herein a polarimetric apparatus where the sample is substantially translucent.

In another particular aspect, there is provided herein a polarimetric apparatus where the sample is substantially reflective.

In another particular aspect, there is provided herein a polarimetric apparatus where the sample is substantially opaque.

In another particular aspect, there is provided herein a polarimetric apparatus where the sample is substantially adjacent to at least one birefringent material.

In another particular aspect, there is provided herein a polarimetric apparatus where the sample is substantially positioned between birefringent materials.

In another particular aspect, there is provided herein a polarimetric apparatus where the sample is a patient's eye or other associated tissue.

In another particular aspect, there is provided herein a polarimetric apparatus where the sample is aqueous humor of a patient's eye.

In another particular aspect, there is provided herein a polarimetric apparatus where the sample is tissue from a skin area of a patient.

In another particular aspect, there is provided herein a polarimetric apparatus where the sample is tissue from a thin-skin area of a patient.

In another particular aspect, there is provided herein a polarimetric apparatus where the sample is tissue from a patient's ear, nose or thin skin between fingers or toes.

In another particular aspect, there is provided herein a polarimetric apparatus where the sample comprises a thin film material.

In another particular aspect, there is provided herein a polarimetric apparatus where the sample comprises a gaseous, liquid or solid material.

In another particular aspect, there is provided herein a polarimetric apparatus where the sample comprises one or more of or of soil, air, and water.

In another particular aspect, there is provided herein a polarimetric apparatus where the substance in the sample comprises glucose in an animal's eye.

In another particular aspect, there is provided herein a polarimetric apparatus where the substance in the sample comprises a cancer cell in an animal.

In another particular aspect, there is provided herein a polarimetric apparatus where the substance in the sample comprises a cancer cell in an animal's skin.

In another particular aspect, there is provided herein a polarimetric apparatus where the substance in the sample comprises a protein or a fragment thereof.

In another particular aspect, there is provided herein a polarimetric apparatus where a noninvasive method for measuring levels of a substance in a sample that may be birefringent in nature in the presence of three dimensional motion comprising:

generating states of polarized light wherein birefringence and retardance are introduced in the polarized light, at least partially interacting with the sample with the birefringed/retarded polarized light, and generating a signal, receiving the a signal obtained by the sample generated by the retarded polarized light, and measuring glucose concentration in the presence of dynamically changing sample birefringence In another particular aspect, there is provided herein a polarimetric apparatus where a non-invasive in vivo method for sensing a concentration of an optically active substance in an animal's eye wherein the method comprises the steps of:

generating states of polarized light wherein birefringence and retardance are introduced in the polarized light, at least partially interacting with the sample with the retarded polarized light, and generating a signal, receiving the a signal obtained by the sample generated by the retarded polarized light, and measuring glucose concentration in the presence of dynamically changing sample birefringence Also, it is within the contemplated scope of the invention herein that commercialized and/or miniaturized versions of the system can be commercially produced for non-invasive polarimetric glucose sensing.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

OTHER REFERENCES

The publication and other material used herein to illuminate the invention or provide additional details respecting the practice of the invention, are incorporated be reference herein, and for convenience are provided in the following bibliography.

NIDDK, *Diabetes Overview*, NIH Publication no. 05-3873, 2005.

N. D. I. Clearinghouse, *Diabetes Statistics*, NIH Publication no. 05-3892, 2004.

N.D. I. Clearinghouse, *Your Guide to Diabetes: Type 1 and Type 2*, NIH Publication no. 05-4016, 2005.

N.D. I. Clearinghouse, *Gestational Diabetes*, NIH Publication no. 04-5129, 2004.

S. Pohjola, "*The glucose content of the aqueous humor in man*," Acta Opthalmol, vol. 88, pp. 11-80, 1966.

B. Rabinovitch, W. F. March and R. L. Adams, "*Noninvasive glucose monitoring of the aqueous humor of the eye. Part I. Measurement of very small optical rotations*," Diabetes Care, vol. 5, pp. 254-258, 1982.

B. Rabinovitch, W. F. March and R. L. Adams, "*Noninvasive glucose monitoring of the aqueous humor of the eye: Part II. Animal studies and the scleral lens*," Diabetes Care, vol. 5, pp. 259-265, 1982.

G. L. Cote, M. D. Fox and R. B. Northrop, "*Noninvasive optical polarimetric glucose sensing using a true phase technique*," IEEE Transactions of Biomedical Engineering, vol. 39, pp. 752-756, 1992.

B. D. Cameron and G. L. Coté, "*Noninvasive glucose sensing utilizing a digital closed-loop polarimetric approach*," IEEE Transactions of Biomedical Engineering, vol. 44, pp. 1221-1227, 1997.

C. Chou, C. Han, W. Kuo, Y. Huang, C. Feng and J. Shyu, "*Noninvasive glucose monitoring in vivo with an optical heterodyne polarimeter*," Applied Optics, vol. 37, no. 16, pp. 3553-3557, 1998.

S. Böckle and L. Rovati and R. R. Ansari, "*Polarimetric Glucose Sensing Using Brewster Reflection of Eye Lens: Theoretical Analysis*," NASA, Glenn Research Center, 2002.

T. W. King, G. L. Coté, R. McNichols and M. J. Goetz, "*Multispectral polarimetric glucose detection using a single pockels cell*," Optical Engineering, vol. 33, pp. 2746-2753, 1994.

B. D. Cameron, "*The application of polarized light to biomedical diagnostics and monitoring*", Ph.D. Dissertation, Texas A&M University, 2000.

B. D. Cameron, H. W. Gorde, B. Satheesan and G. L. Coté, "*The use of polarized laser light through the eye for noninvasive glucose monitoring*," Diabetes Technology & Therapeutics, vol. 1, pp. 135-143, 1999.

B. D. Cameron, S. J. Baba and G. L. Coté, "*Measurement of the glucose transport time delay between the blood and aqueous humor of the eye for the eventual development of a noninvasive glucose sensor*," Diabetes Technology & Therapeutics, vol. 3, pp. 201207, 2001.

S. J. Baba, B. D. Cameron, T. Sangeeta, and G. Cote, "*Effect of temperature, pH, and corneal birefringence on polarimetric glucose monitoring in the eye*," Journal of Biomedical Optics, vol. 7, pp. 321-328, 2002.

B. D. Cameron, U.S. Pat. No. 7,245,952, Noninvasive Birefringence Compensated Glucose Sensing Polarimeter B. D. Cameron and H. Anumula, "Development of a Real-Time Corneal Birefringence Compensated Glucose Sensing Polarimeter," Diabetes Technology & Therapeutics, 8(2) pp. 156-164, 2006.

What is claimed is:

1. A noninvasive polarimetric apparatus used to measure levels of a substance in a sample, in which the sample may exhibit dynamically changing birefringence comprising:
a polarization system configured to generate multiple states of polarized light which interact with a given sample that exhibits dynamically changing birefringence, wherein the polarized light oscillates between left and right circularly polarized light, with elliptically polarized light between the left and right circularly polarized light; and,
an analyzer system configured to receive the resulting signal and generate a secondary signal which can be further processed to measure levels of a substance in the sample, wherein the measured levels provide a measurement of optical activity in relation to analyte concentration.

2. The apparatus of claim 1, wherein one or more of the polarization system and the analyzer system are configured to generate an oscillating birefringence.

3. The apparatus of claim 1, wherein one or more of the polarization system, and the analyzer system comprise a variable retarder.

4. The apparatus of claim 1, wherein one or more of the polarization system and the analyzer system comprise one or more variable retardance modulator systems.

5. The apparatus of claim 1, wherein the light generated exhibits retardation modulation and has a peak retardation modulation depth that corresponds to a quarter of the wavelength of the light being used.

6. The apparatus of claim 1, wherein the frequency of retardation modulation is at a given modulator frequency ($\omega_j$).

7. The apparatus of claim 1, wherein the magnitude and direction of the induced birefringence determine the polarization state of the light exiting the polarization apparatus.

8. The apparatus of claim 1, wherein the polarization system is configured to continuously change the retardance of the polarized light, thus producing continuously changing polarization states.

9. The apparatus of claim 1, wherein the polarimetric apparatus is configured to apply a partial least square (PLS) analysis to the signal.

10. The apparatus of claim 1, wherein the analyzer system is configured to generate a secondary signal that provides predictive information about the sample.

11. The apparatus of claim 1, wherein the analyzer system is configured to receive the signal from the sample in an at least partially transmissive mode.

12. The apparatus of claim 1, wherein the analyzer system is configured to receive the signal from the sample in an at least partially reflectance mode.

13. The apparatus of claim 1, wherein the analyzer system is configured to receive the signal from the sample in an at least partially absorptive mode.

14. The apparatus of claim 1, wherein the substance in a dynamically varying birefringent sample is an optically active substance.

15. The apparatus of claim 1, wherein the substance in the sample causes a refractive index to be measured in the substance.

16. The apparatus of claim 1, wherein the substance in the sample causes absorption data to be measured in the substance.

17. The apparatus of claim 1, wherein the sample comprises a birefringent medium.

18. The apparatus of claim 1, wherein the sample is substantially transparent.

19. The apparatus of claim 1, wherein the sample is substantially translucent.

20. The apparatus of claim 1, wherein the sample is substantially reflective.

21. The apparatus of claim 1, wherein the sample is substantially opaque.

22. The apparatus of claim 1, wherein the sample is substantially adjacent to at least one birefringent material.

23. The apparatus of claim 1, wherein the sample is substantially positioned between birefringent materials.

24. The apparatus of claim 1, wherein the sample is a patient's eye or other associated tissue.

25. The apparatus of claim 1, wherein the sample is aqueous humor of a patient's eye.

26. The apparatus of claim 1, wherein the sample is tissue from a skin area of a patient.

27. The apparatus of claim 1, wherein the sample is tissue from a thin-skin area of a patient.

28. The apparatus of claim 1, wherein the sample is tissue from a patient's ear, nose or thin skin between fingers or toes.

29. The apparatus of claim 1, wherein the sample comprises a gaseous, liquid or solid material.

30. The apparatus of claim 1, wherein the sample comprises one or more of soil, air, and water.

31. The apparatus of claim 1, wherein the substance in the sample comprises glucose in an animal's eye.

32. The apparatus of claim 1, wherein the substance in the sample comprises a protein or a fragment thereof.

33. A noninvasive polarimetric apparatus used to measure levels of a substance in a sample, in which the sample may exhibit dynamically changing birefringence comprising:
   a polarization system configured to generate multiple states of polarized light which interact with a given sample; and,
   an analyzer system configured to receive the resulting signal and generate a secondary signal which can be further processed to measure levels of a substance in the sample;
   wherein the polarization system comprises a first variable retarder modulator, a second variable retarder modulator, and a third variable retarder modulator, and the analyzer system comprises a fourth variable retarder modulator, a fifth variable retarder modulator, and a sixth variable retarder modulator.

34. A noninvasive polarimetric apparatus used to measure levels of a substance in a sample, in which the sample may exhibit dynamically changing birefringence comprising:
   a polarization system configured to generate multiple states of polarized light which interact with a given sample; and,
   an analyzer system configured to receive the resulting signal and generate a secondary signal which can be further processed to measure levels of a substance in the sample;
   wherein the polarization system comprises:
   a first variable retarder modulator having its fast axis oriented at an angle of −45° with respect to an initial vertical linear polarizer,
   a second variable retarder modulator having its fast axis oriented at 45° with respect to the vertical position, and
   a third variable retarder modulator having its fast axis oriented at an angle of 0° with respect to the vertical position; and,
   wherein the analyzer system comprises:
   a fourth variable retarder modulator having its fast axis oriented at an angle of 0° with respect to a vertical position,
   a fifth variable retarder modulator having its fast axis oriented at 45° with respect to the vertical position, and
   a sixth variable retarder modulator having its fast axis oriented at an angle of −45° with respect to the vertical position, and
   a horizontal linear polarizer.

35. A noninvasive polarimetric apparatus used to measure levels of a substance in a sample, in which the sample may exhibit dynamically changing birefringence comprising:
   a polarization system configured to generate multiple states of polarized light which interact with a given sample; and,
   an analyzer system configured to receive the resulting signal and generate a secondary signal which can be further processed to measure levels of a substance in the sample;
   wherein the polarization system comprises:
   a first variable retarder modulator having its fast axis oriented at a $1^{st}$ angle with respect to an initial linear polarizer,
   a second variable retarder modulator having its fast axis oriented at a $2^{nd}$ angle with respect to the first modulator, and
   a third variable retarder modulator having its fast axis oriented at a $3^{rd}$ angle with respect to the second modulator, and,
   wherein the analyzer system comprises:
   a fourth variable retarder modulator having its fast axis oriented at $4^{th}$ angle with respect to the vertical position,
   a fifth variable retarder modulator having its fast axis oriented at a $5^{th}$ angle with respect to the fourth modulator, and
   a sixth variable retarder modulator having its fast axis oriented at a $6^{th}$ angle with respect to the fifth modulator, and
   a linear polarizer.

36. A noninvasive polarimetric apparatus used to measure levels of a substance in a sample, which may be birefringent in nature, having dynamically changing sample birefringence comprising:
   at least one light source,
   at least one vertical polarizer,
   a polarization system configured to generate multiple states of polarized light which interact with a given sample that exhibits dynamically changing birefringence, and
   an analyzer system configured to receive a signal obtained by the sample and generate a secondary signal which may be processed to measure levels of a substance in a sample, wherein the measured levels provide a measurement of optical activity in relation to analyte concentration, and
   at least one horizontal polarizer.

37. A noninvasive polarimetric apparatus used to measure levels of a substance in a sample, in which the sample may exhibit dynamically changing birefringence comprising:
   a polarization system configured to generate multiple states of polarized light which interact with a given sample; and,
   an analyzer system configured to receive the resulting signal and generate a secondary signal which can be further processed to measure levels of a substance in the sample;
   wherein the polarization system comprises a first variable retarder modulator, a second variable retarder modulator, and a third variable retarder modulator, and the analyzer system comprises a fourth variable retarder modulator, a fifth variable retarder modulator, and a sixth variable retarder modulator.

38. A noninvasive polarimetric apparatus used to measure levels of a substance in a sample, in which the sample may exhibit dynamically changing birefringence comprising:
   a polarization system configured to generate multiple states of polarized light which interact with a given sample; and, an analyzer system configured to receive the resulting signal and generate a secondary signal which can be further processed to measure levels of a substance in the sample;

wherein the polarization system comprises a first variable retarder modulator, a second variable retarder modulator, and a third variable retarder modulator, and the analyzer system comprises a fourth variable retarder modulator, a fifth variable retarder modulator, and a sixth variable retarder modulator;

wherein the substance in the sample comprises a cancer cell in an animal.

39. A noninvasive polarimetric apparatus used to measure levels of a substance in a sample, in which the sample may exhibit dynamically changing birefringence comprising:

a polarization system configured to generate multiple states of polarized light which interact with a given sample; and, an analyzer system configured to receive the resulting signal and generate a secondary signal which can be further processed to measure levels of a substance in the sample;

wherein the polarization system comprises a first variable retarder modulator, a second variable retarder modulator, and a third variable retarder modulator, and the analyzer system comprises a fourth variable retarder modulator, a fifth variable retarder modulator, and a sixth variable retarder modulator;

wherein the substance in the sample comprises a cancer cell in an animal's skin.

40. A noninvasive method for measuring levels of a substance in a sample in the presence of dynamically changing birefringence comprising:

generating states of polarized light wherein phase delays are introduced in the polarized light and the polarized light oscillates between left and right circularly polarized light, with elliptically polarized light between the left and right circularly polarized light, at least partially interacting with the sample with the generated polarized light signal(s), wherein the sample exhibits dynamically changing birefringence, receiving a signal obtained by the sample and generating a secondary signal through an analyzer system, and providing a measurement of the levels of the substance in the sample by measuring optical activity in relation to concentration.

41. A non-invasive in vivo method for sensing a concentration of an optically active substance in an animal's eye wherein the method comprises the steps of:

generating states of polarized light wherein phase delays are introduced in the polarized light and the polarized light oscillates between left and right circularly polarized light, with elliptically polarized light between the left and right circularly polarized light, at least partially interacting with the sample with the generated polarized light, receiving a signal obtained by the sample and generating a secondary signal through an analyzer system.

* * * * *